United States Patent [19]
Papay et al.

[11] 4,246,125
[45] Jan. 20, 1981

[54] LUBRICATING OIL AND FUEL COMPOSITION

[75] Inventors: Andrew G. Papay, Manchester; Joseph P. O'Brien, Kirkwood, both of Mo.

[73] Assignee: Edwin Cooper, Inc., St. Louis, Mo.

[21] Appl. No.: 36,075

[22] Filed: May 4, 1979

[51] Int. Cl.$^3$ .............................................. C10M 1/48
[52] U.S. Cl. ...................................... 252/46.6; 44/76
[58] Field of Search .................. 44/76; 252/48.2, 46.6; 260/607 AL

[56] References Cited

U.S. PATENT DOCUMENTS

| | | | |
|---|---|---|---|
| 2,257,969 | 10/1941 | Loane et al. | 260/607 AL |
| 2,956,951 | 10/1960 | Furey . | |
| 3,346,504 | 10/1967 | Herrmann | 260/607AL |
| 3,449,440 | 6/1969 | Anderson | 252/48.2 |

*Primary Examiner*—Patrick Garvin
*Assistant Examiner*—Y. Harris-Smith
*Attorney, Agent, or Firm*—Donald L. Johnson; John F. Sieberth; Joseph D. Odenweller

[57] ABSTRACT

Friction of internal combustion engines is reduced by adding a minor amount of a friction-reducing additive to the lubricating oil or fuel used in such engines. The additive is an aliphatic hydrocarbyl sulfinyl or sulfonyl methane. Performance is enhanced by including a di-lower alkyl $C_{12-36}$ aliphatic hydrocarbyl phosphonate.

12 Claims, No Drawings

LUBRICATING OIL AND FUEL COMPOSITION

BACKGROUND OF THE INVENTION

In order to conserve energy, automobiles are now being engineered to give improved gasoline mileage compared to those in recent years. This effort is of great urgency as a result of Federal regulations recently enacted which compel auto manufacturers to achieve prescribed gasoline mileage. These regulations are to conserve crude oil. In an effort to achieve the required mileage, new cars are being down-sized and made much lighter. However, there are limits in this approach beyond which the cars will not accommodate a typical family.

Another way to improve fuel mileage is to reduce engine friction. The present invention is concerned with this latter approach.

SUMMARY

According to the present invention it has been discovered that engine friction can be lowered by using lubricating oil or fuel containing a minor amount of an aliphatic hydrocarbyl sulfinyl or sulfonyl methane.

DESCRIPTION OF THE PREFERRED EMBODIMENTS

A preferred embodiment of the invention is a friction-reducing additive having the structure

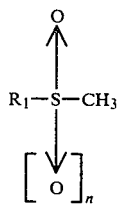

wherein $R_1$ is an aliphatic hydrocarbon group containing about 12–36 carbon atoms and n is 0 or 1.

When n is 0, the additives are aliphatic hydrocarbyl sulfinyl methanes. Examples of these are:
dodecyl sulfinyl methane
dodecenyl sulfinyl methane
1-ethyldodecyl sulfinyl methane
1-octadecyl sulfinyl methane
tetradecyl sulfinyl methane
hexadecyl sulfinyl methane
hexadecenyl sulfinyl methane
2-ethylhexadecyl sulfinyl methane
eicosyl sulfinyl methane
docosyl sulfinyl methane
triacontyl sulfinyl methane
1-hexyltriacontyl sulfinyl methane
1-hexyltriacontenyl sulfinyl methane When n is 1, the additives are aliphatic hydrocarbyl sulfonyl methanes. Examples of these are:
dodecyl sulfonyl methane
dodecenyl sulfonyl methane
1-ethyldodecyl sulfonyl methane
1-octadecyl sulfonyl methane
tetradecyl sulfonyl methane
hexadecyl sulfonyl methane
hexadecenyl sulfonyl methane
2-ethylhexadecyl sulfonyl methane
eicosyl sulfonyl methane
docosyl sulfonyl methane
triacontyl sulfonyl methane
1-hexyltriacontyl sulfonyl methane
1-hexyltriacontenyl sulfonyl methane From the above it can be seen that $R_1$ can be alkyl or alkenyl. Preferably, $R_1$ is an alkyl group. More preferably $R_1$ contains about 14–20 carbon atoms. Still more preferably $R_1$ contains about 16–18 carbon atoms. Most preferably $R_1$ is an alkyl group containing about 16–18 carbon atoms. Examples of these are hexadecyl sulfonyl methane, octadecyl sulfonyl methane, hexadecyl sulfinyl methane, octadecyl sulfinyl methane and mixtures thereof.

The friction-reducing additives are readily made by oxidizing an aliphatic hydrocarbyl methyl sulfide. The aliphatic hydrocarbyl methyl sulfide can be made by reacting an olefinically unsaturated hydrocarbon with methyl mercaptan under uv radiation.

The following examples illustrate how the additives are made.

EXAMPLE 1

In a reaction vessel was placed 166 gms (0.7 mole) of a mixture of $C_{16}$ and $C_{18}$ monoolefin, predominantly straight chain α-olefin. Then 58 gms of methyl mercaptan was added at 35° C. over a 60-minute period while irradiating the glass vessel with uv from a mercury lamp. The product contained excess mercaptan.

In a reaction vessel was placed 198 gms of the above mixture of octadecyl methyl sulfide and hexadecyl methyl sulfide. To this was added a solution of 94 gms (0.83 mole) of 30% hydrogen peroxide dissolved in 79 ml methanol. The reaction was very exothermic and the temperature rose to 80° C. after about 10 ml was added. Addition was stopped and the reaction cooled with an ice bath to 60° C. where it was stirred for a few minutes until reaction subsided. It was then cooled to 44° C. and the rest of the hydrogen peroxide was added dropwise. Total addition time was 40 minutes. The mixture was stirred for 30 minutes at 70° C. and then heated under vacuum to distill off methanol and water. Infrared analysis confirmed the remaining product to be mainly $C_{16-18}$ alkyl sulfinyl methane.

Other aliphatic hydrocarbyl sulfinyl methanes can be made following the above general procedure using different olefins to make the aliphatic hydrocarbyl methyl sulfide.

EXAMPLE 2

In a reaction vessel was placed 100 ml methanol and 126 gms (0.42 mole) of the mixture of hexadecyl methyl sulfoxide and octadecyl methyl sulfoxide made in Example 1. To this was added dropwise a solution of 47 gms of 30% hydrogen peroxide in 47 ml of methanol. Addition took 30 minutes at 40° to 50° C. The mixture was then heated to 70° C. under vacuum to distill off water and methanol leaving a mixture of hexadecyl sulfonyl methane and octadecyl sulfinyl methane.

Other aliphatic hydrocarbyl sulfonyl methane can be made following the above general procedure using different aliphatic hydrocarbyl methyl sulfide made from different olefinic hydrocarbons.

The additives are added to a lubricating oil in an amount which reduces the friction of an engine operating with the oil in the crankcase. A useful concentration is about 0.05–3 wt %. A more preferred range is about 0.1–1.5 wt %.

From the above it can be seen that the present invention provides an improved crankcase lubricating oil. Accordingly, an embodiment of the invention is an improved motor oil composition formulated for use as a crankcase lubricant in an internal combustion engine wherein the improvement comprises including in the crankcase oil an amount sufficient to reduce fuel consumption of the engine of an oil soluble aliphatic hydrocarbyl sulfinyl or sulfonyl methane.

In a highly preferred embodiment such improved motor oil also contains an ashless dispersant, a zinc dialkyldithiophosphonate and an alkaline earth metal salt of a petroleum sulfonic acid or an alkaryl sulfonic acid (e.g. alkylbenzene sulfonic acid).

The additives can be used in mineral oil or in synthetic oils of viscosity suitable for use in the crankcase of an internal combustion engine. Crankcase lubricating oils have a viscosity up to about 80 SUS at 210° F. According to the present invention the additives function to increase fuel economy when added to lubricating oil compositions formulated for use in the crankcase of internal combustion engines. Similar mileage benefits could be obtained in both spark ignited and diesel engines.

Crankcase lubricating oils of the present invention have a viscosity up to about SAE 40. Sometimes such motor oils are given a classification at both 0° and 210° F., such as SAE 10W or SAE 5W 30.

Crankcase lubricants of the present invention can be further identified since they usually contain a zinc dihydrocarbyldithiophosphate in addition to the present additive. Likewise, these crankcase lubricants contain an alkaline earth metal sulfonate such as calcium petroleum sulfonate, calcium alkaryl sulfonate, magnesium petroleum sulfonate, magnesium alkaryl sulfonate, barium petroleum sulfonate, barium alkaryl sulfonate and the like.

Mineral oils include those of suitable viscosity refined from crude oil from all sources including Gulfcoasts, midcontinent, Pennsylvania, California, Alaska and the like. Various standard refinery operations can be used in processing the mineral oil.

Synthetic oil includes both hydrocarbon synthetic oil and synthetic esters. Useful synthetic hydrocarbon oils include liquid polymers of α-olefins having the proper viscosity. Especially useful are the hydrogenated liquid oligomers of $C_{6-12}$ α-olefins such as α-decene trimer. Likewise, alkylbenzenes or proper viscosity can be used, such as didodecylbenzene.

Useful synthetic esters include the esters of both monocarboxylic acid and polycarboxylic acid as well as monohydroxy alkanols and polyols. Typical examples are didodecyl adipate, trimethylol propane tripelargonate, pentaerythritol tetracaproate, di-(2-ethylhexyl)adipate, dilauryl sebacate and the like. Complex esters prepared from mixtures of mono- and dicarboxylic acid and mono- and polyhydroxyl alkanols can also be used.

Blends of mineral oil with synthetic oil are particularly useful. For example, blends of 5-25 wt % hydrogenated α-decene trimer with 75-95 wt % 150 SUS (100° F.) mineral oil results in an excellent lubricant. Likewise, blends of about 5-25 wt % di-(2-ethylhexyl)adipate with mineral oil of proper viscosity results in a superior lubricating oil. Also blends of synthetic hydrocarbon oil with synthetic esters can be used. Blends of mineral oil with synthetic oil are especially useful when preparing low viscosity oil (e.g. SAE 5W 20) since they permit these low viscosities without contributing excessive volatility.

The more preferred lubricating oil composition includes zinc dihydrocarbyldithiophosphate (ZDDP) in combination with the present additives. Both zinc dialkyldithiophosphates and zinc dialkaryldithiophosphates as well as mixed alkyl-aryl ZDDP are useful. A typical alkyl-type ZDDP contains a mixture of isobutyl and isoamyl groups. Zinc dinonylphenyldithiophosphate is a typical aryl-type ZDDP. Good results are achieved using sufficient ZDDP to provide about 0.01-0.5 wt % zinc. A preferred concentration supplies about 0.05-0.3 wt % zinc.

Another additive used in the oil compositions are the alkaline earth metal petroleum sulfonates or alkaline earth metal alkaryl sulfonates. Examples of these are calcium petroleum sulfonates, magnesium petroleum sulfonates, barium alkaryl sulfonates, calcium alkaryl sulfonates or magnesium alkaryl sulfonates. Both the neutral and the overbased sulfonates having base numbers up to about 400 can be beneficially used. These are used in an amount to provide about 0.05-1.5 wt % alkaline earth metal and more preferably about 0.1-1.0 wt %. In a most preferred embodiment the lubricating oil composition contains a calcium petroleum sulfonate or alkaryl (e.g. alkylbenzene) sulfonate.

Viscosity index improvers can be included such as the polyalkylmethacrylate type or the ethylene-propylene copolymer type. Likewise, styrene-diene VI improvers or styrene-acrylate copolymers can be used. Alkaline earth metal salts of phosphosulfurized polyisobutylene are useful.

Most preferred crankcase oils also contain an ashless dispersant such as the polyolefin-substituted succinamides and succinimides of polyethylene polyamines such as tetraethylenepentamine. The polyolefin succinic substituent is preferably a polyisobutene group having a molecular weight of from about 800 to 5,000. Such ashless dispersants are more fully described in U.S. Pat. No. 3,172,892 and U.S. Pat. No. 3,219,666 incorporated herein by reference.

Another useful class of ashless dispersants are the polyolefin succinic esters of mono- and polyhydroxyl alcohols containing 1 to about 40 carbon atoms. Such dispersants are described in U.S. Pat. No. 3,381,022 and U.S. Pat. No. 3,522,179.

Likewise, mixed ester/amides of polyolefin substituted succinic acid made using alkanols, amines and/or aminoalkanols represent a useful class of ashless dispersants.

The succinic amide, imide and/or ester type ashless dispersants may be boronated by reaction with a boron compound such as boric acid. Likewise the succinic amide, imide, and/or ester may be oxyalkylated by reaction with an alkylene oxide such as ethylene oxide or propylene oxide.

Other useful ashless dispersants include the Mannich condensation products of polyolefin-substituted phenols, formaldehyde and polyethylene polyamine. Preferably, the polyolefin phenol is a polyisobutylene-substituted phenol in which the polyisobutylene group has a molecular weight of from about 800 to 5,000. The preferred polyethylene polyamine is tetraethylene pentamine. Such Mannich ashless dispersants are more fully described in U.S. Pat. No. 3,368,972; U.S. Pat. No. 3,413,347; U.S. Pat. No. 3,442,808; U.S. Pat. No. 3,448,047; U.S. Pat. No. 3,539,633; U.S. Pat. No. 3,591,598; U.S. Pat. No. 3,600,372; U.S. Pat. No.

3,634,515; U.S. Pat. No. 3,697,574; U.S. Pat. No. 3,703,536; U.S. Pat. No. 3,704,308; U.S. Pat. No. 3,725,480; U.S. Pat. No. 3,726,882; U.S. Pat. No. 3,736,357; U.S. Pat. No. 3,751,365; U.S. Pat. No. 3,756,953; U.S. Pat. No. 3,793,202; U.S. Pat. No. 3,798,165; U.S. Pat. No. 3,798,247 and U.S. Pat. No. 3,803,039.

The above Mannich dispersants can be reacted with boric acid to form boronated dispersants having improved corrosion properties.

Superior results are obtained by using the present additives in lubricating oil in combination with a phosphonate additive. Preferred phosphonates are the di-$C_{1-4}$ alkyl $C_{12-36}$ alkyl or alkenyl phosphonates. These compounds have the structure:

$$R_2-P\begin{matrix}O\\\|\end{matrix}\begin{matrix}OR_3\\OR_4\end{matrix}$$

wherein $R_2$ is an aliphatic hydrocarbon group containing about 12-36 carbon atoms and $R_3$ and $R_4$ are independently selected from lower alkyl groups containing about 1-4 carbon atoms.

Representative examples of these synergistic coadditives are:
dimethyl octadecylphosphonate
dimethyl octadecenylphosphonate
diethyl 2-ethyldecylphosphonate
ethyl propyl 1-butylhexadecylphosphonate
methyl ethyl octadecylphosphonate
methyl butyl eicosylphosphonate
dimethyl hexatriacontylphosphonate When using the phosphonate coadditive only a small synergistic amount is required. A useful range is about 0.005-0.75 wt % based on the formulated oil. A more preferred amount is about 0.05-0.5 wt %.

The friction reducing additives of this invention are also useful in liquid hydrocarbon fuel compositions. Fuel injected or inducted into a combustion chamber wets the walls of the cylinder. Fuels containing a small amount of the present additive reduce the friction due to the piston rings sliding against the cylinder wall.

The additives can be used in both diesel fuel and gasoline used to operate internal combustion engines. Fuels containing about 0.001-0.25 wt % of the present additives can be used.

Fuels used with the invention can contain any of the additives conventionally added to such fuels. In the case of gasoline it can include dyes, antioxidants, detergents, antiknocks (e.g. tetraethyllead, methylcyclopentadienyl manganese tricarbonyl, rare earth metal chelates, methyl tert-butylether and the like). In the case of diesel fuels the compositions can include pour point depressants, detergents, ignition improvers (e.g. hexylnitrate) and the like.

Tests were conducted which demonstrated the friction reducing properties of the present invention.

LFW-1 TEST

In this test a metal cylinder is rotated around its axis 45° in one direction and then 45° in the opposite direction at a rate of 120 cycles per minute. A metal block curved to conform to the circular contour of the cylinder presses at a fixed load against the periphery of the cylinder. Test lubricant is applied to the rubbing surface between the cylinder and the block. Torque transmitted to the block from the reciprocating cylinder is measured. The greater the torque the greater the friction. Results are given in terms of "percent improvement" which is the percent reduction in torque compared to that obtained with the test oil without the test additive.

SAE-2 FRICTION MACHINE TEST

In this test a heavy fly wheel is rotated at 1440 rpm. A series of 9 clutch plates are then brought to bear axially at a defined load against the fly wheel. The fly wheel is connected to the rotating plates. The stationary plates are connected to a device which measures rotational torque. The time from initially applying pressure through the clutch plate until the rotating plate ceases to rotate is measured. Also, the rotational torque measured at the stationary plates is plotted against time. Torque rises initially to a value referred to as "dynamic torque" and then rises finally to a value called "static torque." The clutch plates are immersed in test lubricant. A reduction in friction is indicated by (1) an increase in time required to bring rotation to a halt and (2) a decrease in dynamic and static torque. Results are reported in percent time increase (percent improvement) and percent reduction in torque compared to that obtained using the same oil without the test additive.

The test oil is a fully formulated oil of SAE SE quality. Test results are given in the following table. In the table the test additive was used at 0.3 wt % and the phosphonate at 0.2 wt %.

|  | % Improvement | | | |
|  |  |  | SAE-2 Torque | |
| Additive | LFW-1 | Time | Dynamic | Static |
| $C_{16-18}$ alkyl sulfonylmethane | 1 | 7 | 5 | 7 |
| $C_{16-18}$ alkyl sulfonylmethane plus octadecyl dimethyl phosphonate | — | 17 | 15 | 29 |
| $C_{16-18}$ alkyl sulfinylmethane | 4 | 7 | 8 | 10 |
| $C_{16-18}$ alkyl sulfinylmethane plus octadecyl dimethyl phosphonate | 9 | 12 | 13 | 28 |

As the above results show the additives of this invention are very effective in reducing friction. Furthermore, their effectiveness is improved by using them in combination with phosphonate.

We claim:
1. A lubricating oil composition containing a major amount of lubricating oil and (1) a minor friction-reducing amount of an additive, said additive having the structure

$$R_1-\underset{[O]_n}{\overset{\overset{\displaystyle O}{\|}}{S}}-CH_3$$

wherein $R_1$ is an aliphatic hydrocarbon group containing about 12–36 carbon atoms and n is 0 or 1, and (2) a promoter amount of a phosphonate coadditive, said phosphonate coadditive having the formula

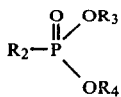

wherein $R_2$ is a $C_{12-36}$ aliphatic hydrocarbon group and $R_3$ and $R_4$ are independently selected from alkyl groups containing 1–4 carbon atoms.

2. A composition of claim 1 wherein $R_3$ and $R_4$ are methyl.

3. A composition of claim 2 wherein n is 0.

4. A composition of claim 2 wherein n is 1.

5. A composition of claim 3 wherein $R_1$ is an alkyl group containing about 16–18 carbon atoms.

6. A composition of claim 5 wherein $R_2$ is octadecyl.

7. A composition of claim 4 wherein $R_1$ is an alkyl group containing about 16–18 carbon atoms.

8. A composition of claim 7 wherein $R_2$ is octadecyl.

9. A liquid hydrocarbon fuel of the gasoline boiling range containing a friction-reducing amount of an additive having the structure

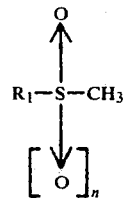

wherein $R_1$ is an aliphatic hydrocarbon group containing about 12–36 carbon atoms and n is 0 or 1.

10. A liquid hydrocarbon fuel of claim 9 wherein $R_1$ contains about 16–18 carbon atoms.

11. A liquid hydrocarbon fuel of claim 10 wherein n is 0.

12. A liquid hydrocarbon fuel of claim 10 wherein n is 1.

* * * * *